United States Patent [19]
Thiele

[11] 4,416,684
[45] Nov. 22, 1983

[54] SYNERGISTIC HERBICIDAL COMPOSITIONS

[75] Inventor: Gerald H. Thiele, Sunnyvale, Calif.

[73] Assignee: Stauffer Chemical Company, Westport, Conn.

[21] Appl. No.: 108,445

[22] Filed: Dec. 31, 1979

Related U.S. Application Data

[63] Continuation-in-part of Ser. No. 26,473, Apr. 2, 1979, abandoned.

[51] Int. Cl.[3] .................. A01N 43/36; A01N 37/00
[52] U.S. Cl. ........................................... 71/95; 71/106
[58] Field of Search .................................. 71/95, 106

[56] References Cited

U.S. PATENT DOCUMENTS

| | | | |
|---|---|---|---|
| 3,434,822 | 3/1969 | Wilson et al. ................. | 71/106 |
| 4,110,105 | 8/1978 | Teach ............................ | 260/326.5 S |
| 4,132,713 | 1/1979 | Broadhurst ................... | 71/95 |
| 4,160,659 | 7/1979 | Rodebush et al. ............ | 71/95 |

Primary Examiner—Glennon H. Hollrah
Attorney, Agent, or Firm—Paul R. Martin; M. Henry Heines

[57] ABSTRACT

Synergistic herbicidal activity is displayed by compositions comprising the following two components:
(a) a pyrrolidone of the formula

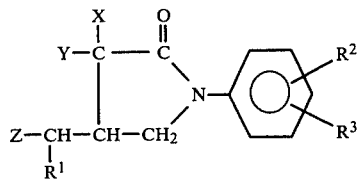

in which
X is selected from the group consisting of hydrogen, chlorine and methyl; Y is selected from the group consisting of hydrogen, chlorine and bromine; Z is selected from the group consisting of chlorine and bromine; $R^1$ is selected from the group consisting of hydrogen and $C_1$-$C_4$ alkyl; $R^2$ is selected from the group consisting of hydrogen, halogen, $C_1$-$C_4$ alkyl, acetyl, trifluoromethyl, nitro, cyano, $C_1$-$C_4$ alkoxy, $C_1$-$C_4$ alkylthio, $C_1$-$C_4$ alkylsulfinyl, $C_1$-$C_4$ alkylsulfonyl, trifluoromethylthio, trifluoromethylsulfinyl, trifluoromethylsulfonyl, pentafluoropropionamido, and 3-methylureido; and
$R^3$ is selected from the group consisting of hydrogen, $C_1$-$C_4$ alkyl, chlorine and trifluoromethyl; and
(b) a m-ureidophenyl carbamate of the formula

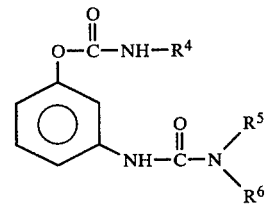

in which $R^4$ is $C_1$-$C_4$ alkyl; $R^5$ is $C_1$-$C_4$ alkyl; and $R^6$ is selected from the group consisting of hydrogen and $C_1$-$C_4$ alkyl, 1t a weight ratio of (a) to (b) of from about 0.1: to about 50:1.

6 Claims, No Drawings

SYNERGISTIC HERBICIDAL COMPOSITIONS

CROSS REFERENCE TO RELATED APPLICATIONS

This is a continuation-in-part of application Ser. No. 26,473, filed Apr. 2, 1979, now abandoned.

BACKGROUND OF THE INVENTION

The protection of crops from weeds and other vegetation which inhibit crop growth by consuming valuable acreage or soil nutrients is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use.

In many cases, active herbicides have been shown to be more effective in combination than when applied individually. The result is often termed "synergism", since the combination demonstrates a potency or activity level exceeding that which it would be expected to have, based on the knowledge of the individual potencies of the components. The present invention resides in the discovery that certain pyrrolidones and certain m-ureidophenyl carbamates already known individually for their herbicidal potency, display this synergistic effect when applied in combination.

PRIOR ART

The two classes of compounds forming the combination which is the subject of the present invention are independently known in the art as active herbicides. Pyrrolidones are disclosed as herbicides in U.S. Pat. No. 4,110,105 (Teach, Aug. 29, 1978), and m-ureidophenyl carbamates are similarly disclosed in U.S. Pat. No. 3,434,822 (Wilson et al., Mar. 25, 1969).

DESCRIPTION OF THE INVENTION

It has now been found that synergism in the control of undesirable vegetation is exhibited by compositions comprising a mixture of the following two components:
(a) a pyrrolidone of the formula

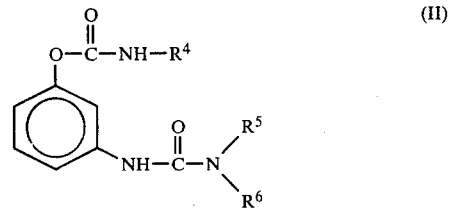

in which
X is selected from the group consisting of hydrogen, chlorine and methyl;
Y is selected from the group consisting of hydrogen, chlorine and bromine;
Z is selected from the group consisting of chlorine and bromine;
$R^1$ is selected from the group consisting of hydrogen and $C_1$–$C_4$ alkyl;
$R^2$ is selected from the group consisting of hydrogen, halogen, $C_1$–$C_4$ alkyl, acetyl, trifluoromethyl, nitro, cyano, $C_1$–$C_4$ alkoxy, $C_1$–$C_4$ alkylthio, $C_1$–$C_4$ alkylsulfinyl, $C_1$–$C_4$ alkylsulfonyl, trifluoromethylthio, trifluoromethylsulfinyl, trifluoromethylsulfonyl, pentafluoropropionamido, and 3-methylureido; and
$R^3$ is selected from the group consisting of hydrogen, $C_1$–$C_4$ alkyl, chlorine and trifluoromethyl; and
(b) a m-ureidophenyl carbamate of the formula

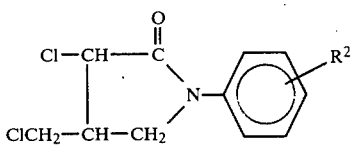

in which
$R^4$ is $C_1$–$C_4$ alkyl;
$R^5$ is $C_1$–$C_4$ alkyl; and
$R^6$ is selected from the group consisting of hydrogen and $C_1$–$C_4$ alkyl.

In the compositions of the present invention, pyrrolidones of the following formula are preferred:

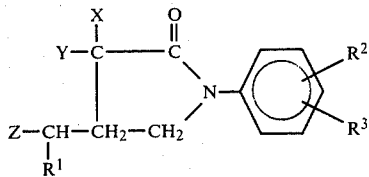

in which $R^2$ is trifluoromethyl or cyano. Preferred m-ureidophenyl carbamates are those in which $R^4$ is $C_1$–$C_4$ alkyl, $R^5$ is $C_1$–$C_2$ alkyl, and $R^6$ is $C_1$–$C_2$ alkyl.

The term "alkyl" as used herein includes both straight-chain and branched-chain groups. The carbon atom ranges stated in this specification are intended to be inclusive of both upper and lower limits.

The terms "synergism" and "synergistic" are used herein to convey the result observed when a combination of two herbicides demonstrates a potency in excess of that which the combination would be expected to produce on the basis of the potencies of each herbicide when applied individually.

The term "herbicide" is used herein to denote a compound which controls or modifies the growth of plants. The term "herbicidally effective amount" is used to indicate the quantity of such a compound or combination of such compounds which is capable of producing a controlling or modifying effect. Controlling or modifying effects include all deviations from natural development, for example, killing, retardation, defoliation, desiccation, regulation, tillering, stunting, stimulating, leaf burn, dwarfing and the like. The term "plants" is used to include germinating seeds, emerging seedlings and established vegetation, including roots and aboveground portions.

In the compositions of this invention, the pyrrolidone:carbamate weight ratio at which the herbicidal response is synergistic lies within the range of about 0.1:1 to about 50:1, preferably about 0.5:1 to about 20:1. Application rates will depend upon the weeds to be controlled and the degree of control desired. In general, the compositions of this invention are most efficiently employed at a rate of 0.01 to 50 pounds per acre (0.011 to 56 kilograms per hectare) of the active ingredient, preferably 0.1 to 25 pounds per acre (0.11 to 28 kilograms per hectare).

Examples of pyrrolidones useful in the present invention are:
1-phenyl-3-chloro-4-chloromethyl-2-pyrrolidone
1-phenyl-3,3-dichloro-4-chloromethyl-2-pyrrolidone
1-(2',6'-dimethylphenyl)-3-chloro-4-chloromethyl-2-pyrrolidone
1-m-chlorophenyl-3-chloro-4-chloromethyl-2-pyrrolidone
1-p-chlorophenyl-3-chloro-4-chloromethyl-2-pyrrolidone
1-m-trifluoromethylphenyl-3-chloro-4-chloromethyl-2-pyrrolidone
1-phenyl-3-chloro-3-methyl-4-chloromethyl-2-pyrrolidone
1-(3',4'-dichlorophenyl)-3,3-dichloro-4-chloromethyl-2-pyrrolidone
1-m-trifluoromethylphenyl-3,3-dichloro-4-chloromethyl-2-pyrrolidone
1-m-trifluoromethylphenyl-3-chloro-3-methyl-4-chloromethyl-2-pyrrolidone
1-p-tolyl-3-chloro-4-chloromethyl-2-pyrrolidone
1-m-fluorophenyl-3-chloro-4-chloromethyl-2-pyrrolidone
1-m-trifluoromethyl-3-bromo-4-bromomethyl-2-pyrrolidone
1-(3',4'-dichlorophenyl)-3-chloro-4-chloromethyl-2-pyrrolidone 1-m-nitrophenyl-3-chloro-4-chloromethyl-2-pyrrolidone
1-(3',5'-dichlorophenyl)-3-chloro-4-chloromethyl-2-pyrrolidone
1-m-trifluoromethylphenyl-3-chloro-4-(1'-chloroethyl)-2-pyrrolidone
1-m-cyanophenyl-3-chloro-4-chloromethyl-2-pyrrolidone
1-(3',5'-dichlorophenyl)-3,3-dichloro-4-chloromethyl-2-pyrrolidone
1-m-trifluoromethylphenyl-3,3-dichloro-4-(1'-chloroethyl)-2-pyrrolidone
1-m-cyanophenyl-3,3-dichloro-4-chloromethyl-2-pyrrolidone
1-(3'-trifluoromethyl-4'-chlorophenyl)-3-chloro-4-chloromethyl-2-pyrrolidone
1-(3'-trifluoromethyl-4'-chlorophenyl)-3,3-dichloro-4-chloromethyl-2-pyrrolidone
1-m-trifluoromethylthiophenyl-3-chloro-4-chloromethyl-2-pyrrolidone
1-m-methylthiophenyl-3-chloro-4-chloromethyl-2-pyrrolidone
1-m-trifluoromethylsulfinylphenyl-3-chloro-4-chloromethyl-2-pyrrolidone
1-m-methylsulfinylphenyl-3-chloro-4-chloromethyl-2-pyrrolidone
1-m-methylsulfonylphenyl-3-chloro-4-chloromethyl-2-pyrrolidone
1-m-trifluoromethylsulfonylphenyl-3-chloro-4-chloromethyl-2-pyrrolidone
1-(3',5'-bis-trifluoromethylphenyl)-3-chloro-4-chloromethyl-2-pyrrolidone
1-m-methoxyphenyl-3-chloro-4-chloromethyl-2-pyrrolidone
1-m-acetylphenyl-3-chloro-4-chloromethyl-2-pyrrolidone
1-m-tolyl-3-chloro-4-chloromethyl-2-pyrrolidone
1-m-trifluoromethylphenyl-4-chloromethyl-2-pyrrolidone
1-m-bromophenyl-3-chloro-4-chloromethyl-2-pyrrolidone
1-o-chlorophenyl-3-chloro-4-chloromethyl-2-pyrrolidone
1-m-iodophenyl-3-chloro-4-chloromethyl-2-pyrrolidone
1-p-methoxyphenyl-3-chloro-4-chloromethyl-2-pyrrolidone
1-o-trifluoromethylphenyl-3-chloro-4-chloromethyl-2-pyrrolidone
1-m-pentafluoropropionamidophenyl-3-chloro-4-chloromethyl-2-pyrrolidone
cis-1-m-trifluoromethylphenyl-3-chloro-4-chloromethyl-2-pyrrolidone
trans-1-m-trifluoromethylphenyl-3-chloro-4-chloromethyl-2-pyrrolidone These and other pyrrolidones within the scope of the invention can be prepared by the procedures described in U.S. Pat. No. 4,110,105.

Examples of m-ureidophenyl carbamates useful in the present invention are:
m-(3,3-dimethylureido)phenyl N-methylcarbamate
m-(3,3-dimethylureido)phenyl N-ethylcarbamate
m-(3,3-dimethylureido)phenyl N-isopropylcarbamate
m-(3,3-dimethylureido)phenyl N-isobutylcarbamate
m-(3,3-dimethylureido)phenyl N-t-butylcarbamate
m-(3,3-dimethylureido)phenyl N-s-butylcarbamate
m-(3,3-dimethylureido)phenyl N-butylcarbamate
m-(3,3-diethylureido)phenyl N-methylcarbamate
m-(3-butyl-3-methylureido)phenyl N-t-butylcarbamate
m-(3,3-diethylureido)phenyl N-t-butylcarbamate
m-(3-methylureido)phenyl N-methylcarbamate
m-(3-ethylureido)phenyl N-ethylcarbamate
m-(3-propylureido)phenyl N-methylcarbamate
m-(3-butylureido)phenyl N-methylcarbamate
m-(3-methylureido)phenyl N-t-butylcarbamate These and other m-ureidophenyl carbamates within the scope of the invention can be prepared by the procedures described in U.S. Pat. No. 3,434,822.

The following examples provide further illustrations, demonstrating the synergistic herbicidal response of the present compositions.

EXAMPLE I

This example demonstrates the synergistic response of 1-m-trifluoromethylphenyl-3-chloro-4-chloromethyl-2-pyrrolidone and m-(3,3-dimethylureido)phenyl t-butylcarbamate in combined postemergence application to a variety of weeds.

Fiber flats measuring 25.4×14.6×7.0 centimeters (cm) were filled to a depth of 5.0 cm with loamy sand soil containing 50 parts per million (ppm) each of the commercial fungicide cis-N[(trichloromethyl)thio]-4-cyclohexene-1,2-dicarboximide (Captan ®) and 18-18-18 fertilizer (percentages of N—$P_2O_5$—$K_2O$ on a weight basis). Several rows were impressed across the width of each flat and each row was seeded with a single weed species. The weed species included yellow nutsedge (*Cyperus esculentus*), wild oat (*Avena fatua*), johnsongrass (*Sorghum halepense*), annual ryegrass (*Lolium multiflorum*), velvetleaf (*Abutilon theophrasti*), jimsonweed (*Datura stramonium*), and annual morning glory (*Ipomoea purpurea*). Ample seeds were planted to give about 20 to 50 seedlings per row after emergence depending on the size of the plants. The flats were then placed in a greenhouse for two weeks, where they were watered regularly.

At the end of this period, the foilage on the emergent weeds was sprayed with aqueous solutions of the test compounds. The solutions were prepared by weighing out appropriate quantities of the test compounds to correspond to the desired application rate in pounds per acre (lb/A) when applied to the flats, and diluting these quantities with water. In control flats, the test compounds were applied alone at various application rates, whereas in the test flats, solutions containing both compounds were applied. Additional flats which were not sprayed at all were used as a standard for measuring the degree of weed control occurring in the treated flats.

Three weeks after treatment, the control and test flats were compared to the standard, and each row was rated visually in terms of percent control ranging from 0% to 100%, with 0% representing the same degree of growth as the same row in the standard and 100% representing complete control of all weeds in the row. All types of weed injury were taken into consideration.

The results of these tests are listed in Table I in the columns headed by the symbol "O", indicating "observed" results. These results are compared with the expected results, shown in the columns headed by the symbol "E" derived from the central data using Limpel's formula (Limpel et al., 1962, "Weed Control of Dimethylchloroterephthalate Alone and in Certain Combinations," Proc. NEWCC, Vol. 16, pp. 48–53):

$$E = X + Y - \frac{XY}{100}$$

where

X = observed percent injury when one of the herbicides is used alone, and

Y = observed percent injury when the other herbicide is used alone.

An asterisk (*) is used to indicate the tests where the results show synergism, i.e., where the observed result exceeds the expected result. Since synergism can only be detected when the expected result is less than 100, tests where both the E and O values are 100 are left blank. It is clear from the table that synergism was evident in most of the tests run.

TABLE I
HERBICIDE SYNERGISM TEST RESULTS

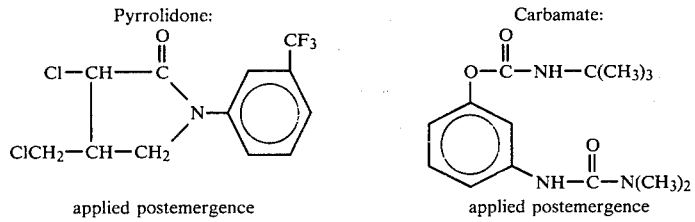

Pyrrolidone: applied postemergence

Carbamate: applied postemergence

| Application Rates (lb/A) | | Johnson-grass | | Ryegrass | | Morning-glory | | Wild Oat | | Nutsedge | | Jimson-weed | | Velvet-leaf | |
|---|---|---|---|---|---|---|---|---|---|---|---|---|---|---|---|
| Pyrrolidone | Carbamate | O | E | O | E | O | E | O | E | O | E | O | E | O | E |
| Control Data: | | | | | | | | | | | | | | | | |
| 0.125 | — | 0 | | 0 | | 0 | | 0 | | 0 | | 100 | | 60 | |
| 0.25 | — | 0 | | 0 | | 0 | | 0 | | 0 | | 40 | | 75 | |
| 0.5 | — | 30 | | 0 | | 0 | | 40 | | 0 | | 100 | | 80 | |
| — | 0.05 | 0 | | 0 | | 30 | | 0 | | 0 | | 100 | | 0 | |
| — | 0.125 | 0 | | 40 | | 100 | 100 | | | 100 | 0 | 0 | 100 | | 100 | |
| — | 0.25 | 50 | | 95 | | 100 | | 100 | | 0 | | 100 | | 100 | |
| Test Data: | | | | | | | | | | | | | | | | |
| 0.125 | 0.05 | 0 | 0 | 0 | 0 | 100* | 30 | 0 | 0 | 0 | 0 | | | 100* | 60 |
| 0.125 | 0.125 | 100* | 0 | 100* | 40 | | | | | 0 | 0 | | | | |
| 0.125 | 0.25 | 100* | 50 | 100* | 95 | | | | | 0 | 0 | | | | |
| 0.25 | 0.05 | 60* | 0 | 100* | 0 | 100* | 30 | 100* | 0 | 0 | 0 | | | 100* | 75 |
| 0.25 | 0.125 | 60* | 0 | 100* | 40 | | | | | 50* | 0 | | | | |
| 0.25 | 0.25 | 100* | 50 | 100* | 95 | | | | | 10* | 0 | | | | |
| 0.5 | 0.05 | 100* | 30 | 100* | 0 | 100* | 30 | 100* | 40 | 20* | 0 | | | 100* | 80 |
| 0.5 | 0.125 | 100* | 30 | 100* | 40 | | | | | 10* | 0 | | | | |
| 0.5 | 0.25 | 100* | 86 | 100* | 95 | | | | | 65* | 0 | | | | |

*Synergistic effect shown.
Blank spaces indicate 100% control in both observed and expected results, precluding evaluation of synergism.

EXAMPLE II

The tests shown in this example were performed with the same herbicides used in Example I. The application rates were lower, however, and the compounds were applied in pre-emergence fashion, i.e., they were sprayed over the soil surface immediately after the seeds were planted, rather than after the weeds had emerged from the soil. The planting flats were made of aluminum and the weed species tested were wild oat (*Avena fatua*), annual morning glory (*Ipomoea purpurea*), yellow nutsedge (*Cyperus esculentus*), annual ryegrass (*Lolium multiflorum*), shattercane (*Sorghum bicolor*), foxtail (*Setaria lutescens*), prickly sida (*Sida spinosa*), and velvetleaf (*Abutilon theophrasti*). Injury ratings were taken after 4 weeks.

The results of these tests are shown in Tables II and III, where synergism is evident throughout.

TABLE II

HERBICIDE SYNERGISM TEST RESULTS

Pyrrolidone:

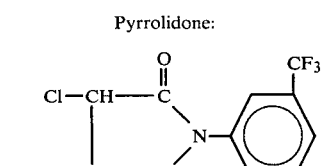

pre-emergence application

Carbamate:

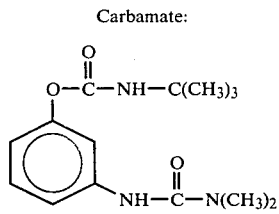

pre-emergence application

| Application Rates (lb/A) | | Percent Control - O: Observed E: Expected | | | | | | | |
|---|---|---|---|---|---|---|---|---|---|
| | | Wild Oat | | Morning-glory | | Nutsedge | | Ryegrass | |
| Pyrrolidone | Carbamate | O | E | O | E | O | E | O | E |
| Control Data: | | | | | | | | | |
| 0.06 | — | 0 | | 0 | | 0 | | 30 | |
| 0.13 | — | 60 | | 10 | | 10 | | 60 | |
| 0.25 | — | 95 | | 30 | | 40 | | 100 | |
| — | 0.025 | 60 | | 0 | | 0 | | 0 | |
| — | 0.05 | 75 | | 30 | | 0 | | 10 | |
| — | 0.075 | 100 | | 100 | | 0 | | 60 | |
| — | 0.1 | 100 | | 100 | | 0 | | 70 | |
| Test Data: | | | | | | | | | |
| 0.06 | 0.025 | 100* | 60 | 100* | 0 | 0 | 0 | 40* | 30 |
| 0.06 | 0.05 | 60 | 75 | 100* | 30 | 0 | 0 | 50* | 37 |
| 0.06 | 0.075 | | | | | 0 | 0 | 98* | 72 |
| 0.06 | 0.1 | | | | | 0 | 0 | 98* | 79 |
| 0.13 | 0.025 | 100* | 84 | 100* | 10 | 30* | 10 | 70* | 60 |
| 0.13 | 0.05 | 95* | 90 | 40* | 37 | 60* | 10 | 75* | 64 |
| 0.13 | 0.075 | | | | | 60* | 10 | 100* | 84 |
| 0.13 | 0.1 | | | | | 65* | 10 | 100* | 88 |
| 0.25 | 0.025 | | | 100* | 30 | 65* | 40 | | |
| 0.25 | 0.05 | | | 100* | 51 | 65* | 40 | | |
| 0.25 | 0.075 | | | | | 70* | 40 | | |
| 0.25 | 0.1 | | | | | 70* | 40 | | |

*Synergistic effect shown.
Blank spaces indicate 100% control in both observed and expected results, precluding evaluation of synergism.

TABLE III

HERBICIDE SYNERGISM TEST RESULTS

Pyrrolidone:

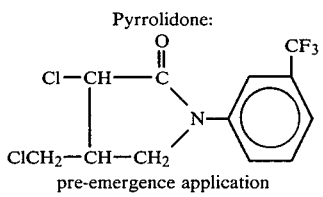

pre-emergence application

Carbamate:

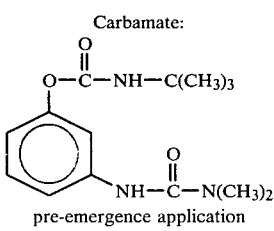

pre-emergence application

| Application Rates (lb/A) | | Percent Control - O: Observed E: Expected | | | | | | | |
|---|---|---|---|---|---|---|---|---|---|
| Pyrrolidone | Carbamate | Shattercane | | Foxtail | | Prickly Sida | | Velvetleaf | |
| Control Data: | | | | | | | | | |
| 0.06 | — | 0 | | 100 | | 0 | | 0 | |
| 0.13 | — | 75 | | 100 | | 30 | | 40 | |
| 0.25 | — | 100 | | 100 | | 70 | | 100 | |
| — | 0.025 | 0 | | 0 | | 40 | | 20 | |
| — | 0.05 | 0 | | 0 | | 60 | | 100 | |
| — | 0.075 | 10 | | 50 | | 65 | | 100 | |
| — | 0.1 | 20 | | 90 | | 70 | | 100 | |
| Test Data: | | | | | | | | | |
| 0.06 | 0.025 | 0 | 0 | | | 60* | 40 | 100* | 20 |
| 0.06 | 0.05 | 20* | 0 | | | 65* | 60 | | |
| 0.06 | 0.075 | 50* | 10 | | | 70* | 65 | | |
| 0.06 | 0.1 | 60* | 20 | | | 100* | 70 | | |
| 0.13 | 0.025 | 100* | 75 | | | 70* | 58 | 100* | 52 |
| 0.13 | 0.05 | 100* | 75 | | | 75* | 72 | | |
| 0.13 | 0.075 | 100* | 78 | | | 90* | 76 | | |
| 0.13 | 0.1 | 100* | 80 | | | 100* | 79 | | |
| 0.25 | 0.025 | | | | | 100* | 82 | | |
| 0.25 | 0.05 | | | | | 100* | 88 | | |
| 0.25 | 0.075 | | | | | 95* | 90 | | |
| 0.25 | 0.1 | | | | | 100* | 91 | | |

*Synergistic effect shown.
Blank spaces indicate 100% control in both observed and expected results, precluding evaluation of synergism.

EXAMPLE III

The tests shown in this example were performed with 1-m-cyanophenyl-3-chloro-4-chloromethyl-2-pyrrolidone and m-(3,3-dimethylureido)phenyl t-butylcarbamate. Fiber flats were used and the weed species were wild oat (*Avena fatua*), yellow nutsedge (*Cyperus esculentus*), annual morning glory (*Ipomoea purpurea*), red oat (*Avena sativa*), annual ryegrass (*Lolium multiflorum*), and nightshade (*Solanum sp.*). In the first test, the results of which are shown in Table IV, pre-emergence application was used. Injury ratings were taken twenty days after seeding and treatment. In the second test, postemergence application was used. Treatment was done ten days after seeding, and injury ratings were taken seventeen days later.

These tests were performed during the winter season when normal growth rates were reduced. As a result, plant injury was more difficult to detect and the injury ratings were consequently lower. Synergism was evident in many of the tests, however, as the results show.

TABLE IV
HERBICIDE SYNERGISM TEST RESULTS

Pyrrolidone: 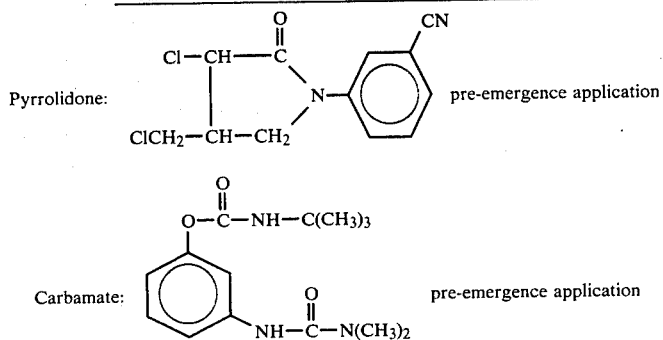 pre-emergence application

Carbamate: pre-emergence application

| Application Rates (lb/A) | | Percent Control - O: Observed E: Expected | | | | | | | | | | | |
|---|---|---|---|---|---|---|---|---|---|---|---|---|---|
| | | Wild Oat | | Nut-sedge | | Morning-glory | | Red Oat | | Rye-grass | | Night-shade | |
| Pyrrol-idone | Car-bamate | O | E | O | E | O | E | O | E | O | E | O | E |
| Control Data: | | | | | | | | | | | | | |
| 0.062 | — | 0 | | 0 | | 0 | | 0 | | 0 | | 0 | |
| 0.125 | — | 0 | | 0 | | 0 | | 0 | | 0 | | 0 | |
| 0.25 | — | 0 | | 0 | | 10 | | 0 | | 0 | | 30 | |
| — | 0.025 | 0 | | 0 | | 0 | | 0 | | 0 | | 0 | |
| — | 0.050 | 0 | | 0 | | 0 | | 0 | | 0 | | 0 | |
| — | 0.075 | 15 | | 0 | | 0 | | 20 | | 0 | | 10 | |
| Test Data: | | | | | | | | | | | | | |
| 0.062 | 0.025 | 0 | 0 | 0 | 0 | 0 | 0 | 0 | 0 | 0 | 0 | 0 | 0 |
| 0.062 | 0.050 | 0 | 0 | 0 | 0 | 0 | 0 | 0 | 0 | 0 | 0 | 0 | 0 |
| 0.062 | 0.075 | 20* | 15 | 0 | 0 | 0 | 0 | 0 | 20 | 0 | 0 | 0 | 10 |
| 0.125 | 0.025 | 0 | 0 | 0 | 0 | 10* | 0 | 0 | 0 | 0 | 0 | 0 | 0 |
| 0.125 | 0.050 | 30* | 0 | 0 | 0 | 10* | 0 | 0 | 0 | 0 | 0 | 0 | 0 |
| 0.125 | 0.075 | 65* | 15 | 0 | 0 | 20* | 0 | 0 | 20 | 0 | 0 | 10 | 10 |
| 0.25 | 0.025 | 30* | 0 | 0 | 0 | 0 | 10 | 0 | 0 | 0 | 0 | 100* | 30 |
| 0.25 | 0.050 | 60* | 0 | 0 | 0 | 10 | 10 | 0 | 0 | 0 | 0 | 100* | 30 |
| 0.25 | 0.075 | 70* | 15 | 0 | 0 | 20* | 10 | 10 | 20 | 0 | 0 | 100* | 37 |

*Synergistic effect shown.

TABLE V
HERBICIDE SYNERGISM TEST RESULTS

Pyrrolidone: 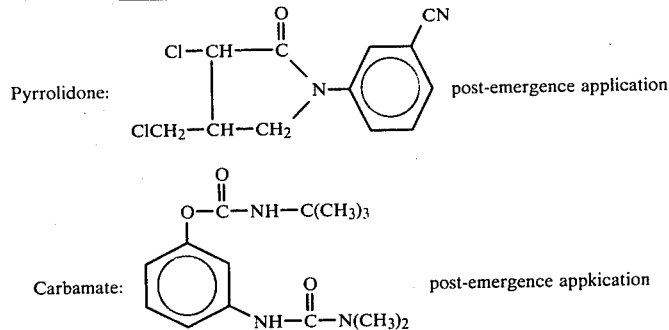 post-emergence application

Carbamate: post-emergence appkication

| Application Rates (lb/A) | | Percent Control - O: Observed E: Expected | | | | | | | | | | | |
|---|---|---|---|---|---|---|---|---|---|---|---|---|---|
| | | Wild Oat | | Water grass | | Nut-sedge | | Morning-glory | | Rye-grass | | Foxtail | |
| Pyrrol-idone | Car-bamate | O | E | O | E | O | E | O | E | O | E | O | E |
| Control Data: | | | | | | | | | | | | | |
| 0.062 | — | 0 | | 0 | | 0 | | 0 | | 0 | | 0 | |
| 0.125 | — | 0 | | 0 | | 0 | | 0 | | 0 | | 0 | |
| 0.25 | — | 0 | | 0 | | 0 | | 0 | | 0 | | 30 | |
| — | 0.025 | 0 | | 0 | | 0 | | 0 | | 0 | | 0 | |
| — | 0.050 | 10 | | 0 | | 0 | | 0 | | 0 | | 0 | |
| — | 0.075 | 40 | | 0 | | 0 | | 0 | | 30 | | 20 | |
| Test Data: | | | | | | | | | | | | | |
| 0.062 | 0.025 | 0 | 0 | 0 | 0 | 0 | 0 | 100* | 0 | 10* | 0 | 75* | 0 |
| 0.062 | 0.050 | 0 | 10 | 0 | 0 | 0 | 0 | 90* | 0 | 30* | 0 | 100* | 0 |
| 0.062 | 0.075 | 60* | 40 | 0 | 0 | 0 | 0 | 100* | 0 | 50* | 30 | 100* | 20 |
| 0.125 | 0.025 | 0 | 0 | 0 | 0 | 0 | 0 | 40* | 0 | 20* | 0 | 40* | 0 |
| 0.125 | 0.050 | 30 | 10 | 0 | 0 | 0 | 0 | 80* | 0 | 30* | 0 | 40* | 0 |

TABLE V-continued
HERBICIDE SYNERGISM TEST RESULTS

Pyrrolidone: 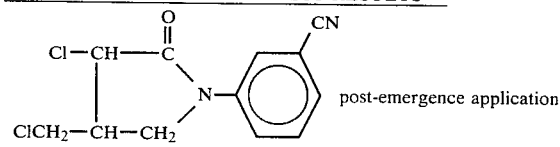 post-emergence application

Carbamate: 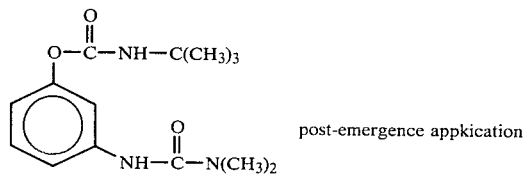 post-emergence appkication

| Application Rates (lb/A) | | Percent Control - O: Observed E: Expected | | | | | | | | | | |
|---|---|---|---|---|---|---|---|---|---|---|---|---|
| | | Wild Oat | | Water grass | | Nut-sedge | | Morning-glory | | Rye-grass | | Foxtail | |
| Pyrrol-idone | Car-bamate | O | E | O | E | O | E | O | E | O | E | O | E |
| 0.125 | 0.075 | 65* | 40 | 0 | 0 | 0 | 0 | 100* | 0 | 30 | 30 | 100* | 20 |
| 0.25 | 0.025 | 0 | 0 | 0 | 0 | 0 | 0 | 95* | 0 | 0 | 0 | 30 | 30 |
| 0.25 | 0.050 | 10 | 10 | 0 | 0 | 0 | 0 | 85* | 0 | 0 | 0 | 100* | 30 |
| 0.25 | 0.075 | 80* | 40 | 65* | 0 | 0 | 0 | 100* | 0 | 40* | 30 | 100* | 44 |

*Synergistic effect shown.

The compositions of this invention are useful as herbicides demonstrating synergistic activity for the control of undesirable vegetation. The compositions can be formulated in the same manner in which herbicides are generally formulated. The compounds may be applied either separately or combined as part of a two-part herbicidal system.

The object of the formulation is to apply the compositions to the locus where control is desired by a convenient method. The "locus" may include soil, seeds, seedlings, and vegetation.

Formulations will generally contain several additives. Among these are some inert ingredients and diluent carriers such as organic solvents, water, oil and water, water in oil emulsions, carriers of dust and granules, and surface active, wetting, dispersing, and emulsifying agents.

Fertilizers, e.g., ammonium nitrate, urea and superphosphate may also be added.

Aids to rooting and growth, e.g., compost, manure, humus, sand, etc., may likewise be added.

The formulations are commonly dusts, wettable powders, granules, solutions of emulsifiable concentrates.

Dusts are free-flowing powder compositions containing the herbicidal compound impregnated on a particulate carrier. The particle size of the carrier is usually in the approximate range of 30 to 50 microns. Examples of suitable carriers are talc, bentonite, diatomaceous earth, and pyrophyllite. Anticaking and antistatic agents can be added, if desired. The composition generally contains up to 50% of active ingredient. Dusts, like liquid compositions, can be applied from boom and hand or power sprayers or airplanes.

Wettable powders are finely divided compositions comprising a particulate carrier impregnated with the herbicide compound and additionally containing one or more surface active agents. The surface active agent promotes rapid dispersion of the powder in aqueous medium to form stable, sprayable suspensions. A wide variety of surface active agents can be used, for example, long chain fatty alcohols; salts of sulfonic acid; esters of long chain fatty acids; and polyhydric alcohols; in which the alcohol groups are free, omega-substituted polyethylene glycols of relatively long chain length. A list of surface active agents suitable for use in agriculture formulations can be found in Wade Van Valkenburg, *Pesticide Formulations*, (Marcel Dekker, Inc., N.Y., 1973) at pages 79–84.

Granules comprise the herbicidal composition impregnated on a particulate inert carrier having a particle size of about 1 to 2 millimeters in diameter. The granules can be made by spraying a solution of the active ingredient in a volatile solvent onto the granular carrier. Suitable carriers in preparation of granules include clay, vermiculite, sawdust, granular carbon, etc.

The herbicidal compositions can also be applied to the soil in the form of a solution in a suitable solvent. Solvents frequently used in herbicidal formulations include kerosene, fuel oil, xylene, petroleum fractions with boiling ranges above xylene, and aromatic petroleum fractions rich in methylated naphthalenes.

Emulsifiable concentrates consist of an oil solution of the herbicide along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate.

It is not necessary that the compositions be admixed with the soil particles. After application by the above discussed methods, they may be distributed below the surface to a depth of at least one-half inch by conventional means such as discing, dragging, or mixing.

The compositions of this invention can also be applied by addition to irrigation water supplied to the field to be treated. This method of application permits the penetration of the compositions into the soil as the water is absorbed therein.

What is claimed is:

1. A synergistic herbicidal composition consisting essentially of a mixture of
   (a) an effective amount of a pyrrolidone of the formula

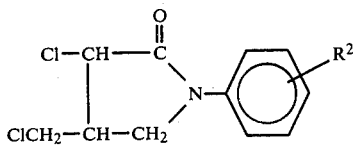

in which $R^2$ is trifluoromethyl or cyano, and
(b) an effective amount of a m-ureidophenyl carbamate of the formula

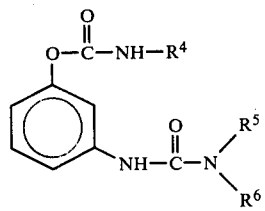

in which
$R^4$ is $C_1$–$C_4$ alkyl,
$R^5$ is $C_1$–$C_2$ alkyl, and
$R^6$ is $C_1$–$C_2$ alkyl,
   at a weight ratio of (a) to (b) of from about 0.5:1 to about 20:1.

2. A composition according to claim 1 in which $R^2$ is m-trifluoromethyl, $R^4$ is t-butyl, $R^5$ is methyl, and $R^6$ is methyl.

3. A composition according to claim 1 in which $R^2$ is m-cyano, $R^4$ is t-butyl, $R^5$ is methyl, and $R^6$ is methyl.

4. A method of controlling undesirable vegetation which comprises applying to the locus where control is desired an herbicidal composition consisting essentially of a mixture of
   (a) an effective amount of a pyrrolidone of the formula

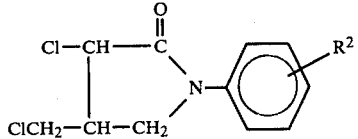

in which $R^2$ is trifluoromethyl or cyano, and
(b) an effective amount of a m-ureidophenyl carbamate of the formula

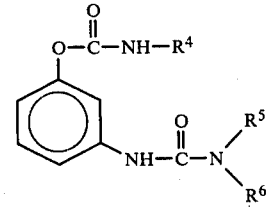

in which
$R^4$ is $C_1$–$C_4$ alkyl,
$R^5$ is $C_1$–$C_2$ alkyl, and
$R^6$ is $C_1$–$C_2$ alkyl,
   at a weight of (a) to (b) of from about 0.5:1 to about 20:1.

5. A method according to claim 4 in which $R^2$ is m-trifluoromethyl, $R^4$ is t-butyl, $R^5$ is methyl, and $R^6$ is methyl.

6. A method according to claim 4 in which $R^2$ is m-cyano, $R^4$ is t-butyl, $R^5$ is methyl, and $R^6$ is methyl.

* * * * *